United States Patent [19]

Singh

[11] Patent Number: 5,649,933
[45] Date of Patent: Jul. 22, 1997

[54] CIRCUMCISION CLAMP

[76] Inventor: Gurchran Singh, 146, Lorong Maarof, Bukit Bandaraya, 59000 Kuala Lumpur, Malaysia

[21] Appl. No.: 325,241

[22] PCT Filed: Apr. 19, 1993

[86] PCT No.: PCT/GB93/00814

§ 371 Date: Feb. 13, 1995

§ 102(e) Date: Feb. 13, 1995

[87] PCT Pub. No.: WO93/20766

PCT Pub. Date: Oct. 28, 1993

[30] Foreign Application Priority Data

Apr. 20, 1992 [MY] Malaysia .............. PI 9200661
Mar. 9, 1993 [MY] Malaysia .............. PI 9300413

[51] Int. Cl.[6] ................................................ A61B 17/32
[52] U.S. Cl. ...................................... 606/118; 606/157
[58] Field of Search .................... 606/118–157, 221

[56] References Cited

U.S. PATENT DOCUMENTS

| 2,646,046 | 7/1953 | Maryan | 606/118 |
| 3,111,124 | 11/1963 | Rodbard | 606/118 |
| 3,625,218 | 12/1971 | Valinoti, Jr. | |
| 3,789,848 | 2/1974 | Honjyo | 606/118 |
| 4,491,136 | 1/1985 | LeVeen | 606/118 |

FOREIGN PATENT DOCUMENTS

| 40407154 | 3/1992 | Japan | 606/118 |
| 1379374 | 1/1975 | United Kingdom . | |

OTHER PUBLICATIONS

Paper by Dr. H.S. Yellen: Gomro Bloodless Circumcision Clamp Jan. 23, 1935.

*Primary Examiner*—Robert A. Hafer
*Assistant Examiner*—Justine Yu
*Attorney, Agent, or Firm*—Clifford W. Browning; Woodard, Emhardt, Naughton Moriarty & McNett

[57] ABSTRACT

A circumcision clamp comprising a clamping ring (5) displaceably mounted on a tubular support (9) having a flared end section (12) for internal reception of the glans penis and external envelopment by the prepuce. The clamping ring is movable between an open position defining a prepuce-receiving gap and a closed position in which the gap is closed, and locking means (13, 18) for locking the clamping ring (5) in the closed position.

3 Claims, 3 Drawing Sheets

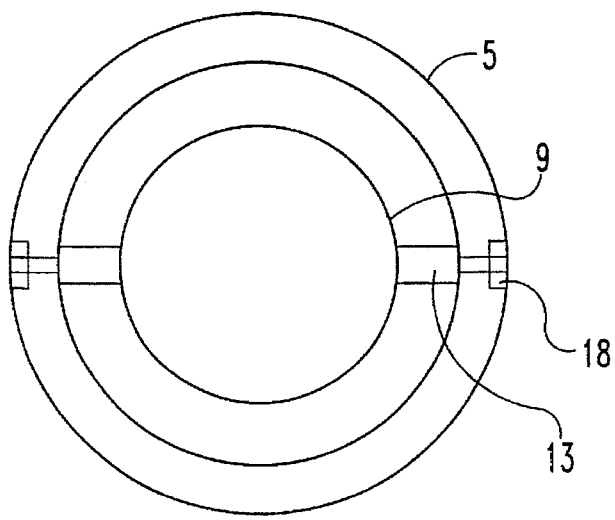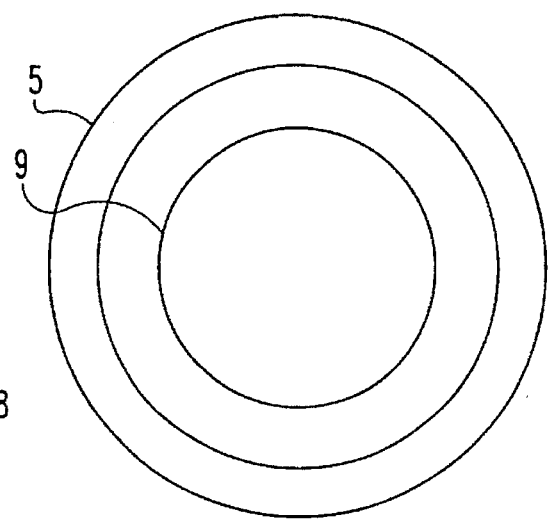
Fig. 5
Fig. 6
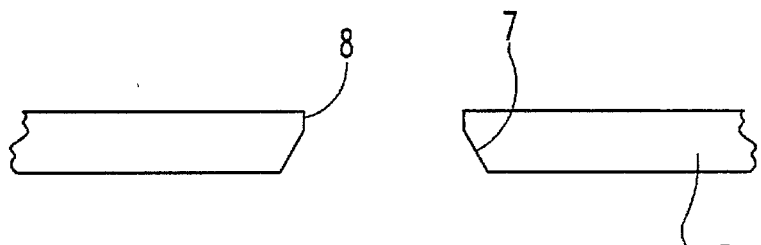
Fig. 10
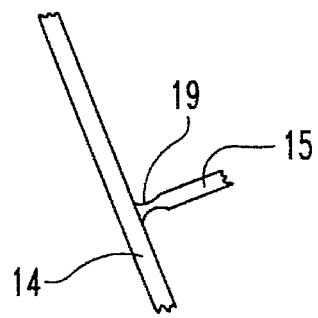
Fig. 9

CIRCUMCISION CLAMP

This invention relates to a circumcision clamp.

Circumcision involves surgical removal of the foreskin or prepuce of the penis. Although it is a minor operation it still too often becomes time-consuming and bloody.

The common practice, generally, in carrying out circumcision, even today, is to use surgical scissors to cut the foreskin. The trimming obtain is usually not only crude and rough but also causes bleeding and needs sutures to be applied to the cut edges. Generally, sterilised gauze and dressing are also applied and sometimes antibiotics may have to be prescribed to prevent infection. Also, undue or unusual loss of tissue due to simple excessive excision, sometimes amounting to accidental amputation of the penis have been mentioned in the literature.

In the prior art, there is a number of instruments known for performing circumcision operations. For practical purposes, many are complex to operate and have an undesirably large number of parts which are either detached from each other or need several auxiliary instruments in operation.

A number of such instruments involve clamping. This is attained by tightening a clamp at the desired position on the prepuce by a screw mechanism. In such screw devices the screw has to be manipulated or turned gradually until occlusion of the prepuce has been achieved. This, therefore, does not achieve an "instant occlusion" at the site of clamping. Also, soon after the circumcision has been performed, the clamp is dismantled and removed. The exposed cut edges generally need to be sutured and aseptic dressing has to be applied. The wound has to be closely watched for infection, bleeding and oozing for the next few days.

Some of the prior instruments involve clamping by applying a tight ligature to a bell shaped device which is fitted over the glans. The foreskin is stretched over this and a ligature is applied at the base. The distal foreskin is then excised and the base of the device is left in situ until it drops off in a few days. Complications such as bleeding, infection and oozing have also been reported.

Some circumcision tools involve using a ring-clamp. As the penis is almost always in a naturally flaccid state because of apprehension and fear whenever a circumcision is performed, the ring-clamp being used to clamp the foreskin may just fit the flaccid penis. A narrow ring-clamp does sometimes pose problems when the penis has an erection. Such erections generally occur in the mornings. During an erection, as the circumference and length of the penis increases, such a ring-clamp may become tight and cause some degree of constriction at the operated site. As a result, such erections present a major problem after operation and cause some discomfort and in some cases considerable pain, at the operated site. Also in cases where sutures have been applied, such erections also put tension on the suture line and cause considerable pain.

The present invention is an improvement and overcomes the above noted circumcision problems associated with heretofore available clamps. It is designed to allow for instant clamping of the foreskin at the desired level. Such clamping produces an instant, total and complete occlusion of the blood and nerve supply to the foreskin which is distal to the site of occlusion. As a result, minimal pain is felt and there is hardly any lingering pain after the circumcision has been performed. It also diminishes the fear, anxiety and apprehension associated with circumcision. Complete haemostasis and infection prevention, until the operated site has healed are other benefits derived from this invention. The design also prevents constriction at the operated site when the penis has an erection.

The instrument is of a simple design and is plastic based. It is pre-sterilised and is individually packed in a sterile packing. It is meant for single use only and is entirely disposed of after use.

Since each circumcision tool is supplied in a sealed sterile packing and is meant for single use only, the need, therefore, to predetermine the right size of the tool, for use, for any individual (from infants to adults) becomes necessary and imperative. In the prior art, there is no such device for this purpose. To achieve this, a separate disposable measuring device is provided. Thus, unnecessary opening and hence contamination of several sealed packings, to choose the right size of the circumcision tool, for any individual, is avoided.

Amongst the main objects of this invention, therefore is to present an invention which relates, most fittingly, to the present day concept of convenient, easy to use and 'use once and throw away' surgical instruments. The other objects are as follows:

1. It is the general object of this invention to provide an instrument which helps to obtain an occlusion which is not only complete, both annularly and also throughout the entire thickness of the prepuce but one that can also continue to maintain such an occlusion in this state, even after the circumcision has been performed without any need for dismantling or further manipulation of any part of the tool at all, until it drops off, by itself, when the surgical wound has healed. There is, thus, no danger of separation of the skin and mucosal layers. The occlusion thus obtained and maintained, keeps the cut ends firmly apposed completely and this forms a natural barrier to any contamination or infection and prevents any bleeding or oozing from the operated site.

2. Another object, is to allow for complete disposal of the tool after use so that there is no danger of cross-infection arising from re-use of the same tool.

3. Another object, is to help obtain the fastest performance of safe, clean, aseptic, bloodless, sutureless and almost painless circumcision.

4. Another object is to keep the cut ends firmly apposed and in the initial stretched state as existing at the time when the prepuce was excised, until the wound has healed so that there is very little contraction of the healed end, i.e. when the scar eventually develops.

5. Another object is to provide an instrument of a simple design so that it can be used with minimal and easy to follow simple steps.

6. A further object is to provide an instrument, which has an irreversible and unbreakable latch, so that when the instrument has dropped off the penis after the wound has healed, it cannot be reused.

7. A further object is to avoid any necessity of any dressing to be applied to the site of surgery.

8. Another object is to provide an instrument that does not cause constriction at the operated site whenever the penis has an erection. This instrument avoids this constriction by having a tubular member which limits the increase in the size of the glans circumferentially but not longitudinally. This limitation along the entire length of the glans prevents any constriction at the operated site. The tubular member besides covering the glans circumferentially is also slightly longer than the average length of the flaccid glans.

9. A further object is to provide an instrument which has a tubular component to cover the glans circumferentially so as to prevent the stretching of the surgical wound during penile erections and the consequent pain at the site of surgery while the healing is taking place.

10. A further object is to provide a tubular component that covers the glans circumferentially only and not at the urethral opening so that urine may be voided whenever necessary without hindrance.

Although there are other incidental objects in view, the above shows that this invention has a number of marked improvements which will distinguish it from the other known instruments used for circumcision.

In order that the present invention may be readily understood, the following description is given. Reference will also be made to the following drawings.

In the annexed drawings,

FIG. 5 is a plan view of the clamp taken along line 2—2 of FIG. 4;

FIG. 6 is a bottom view of the clamp taken along line 3—3 of FIG. 4;

FIG. 9 shows an enlarged fragmentary cross-section view of the design of the flexible hinge joint between the short limb and the clamping arm, and FIG. 10 shows an enlarged fragmentary cross-section view of the rim of the circular opening of the outer member.

The present invention relates to two apparatus which cofunction and complement each other in the performance of circumcision. The first apparatus helps to determine the selection of the right size of the second apparatus suitable for use for any individual (from infants to adults). The first apparatus is a disposable measuring device and the second apparatus is a disposable circumcision tool. The second apparatus is packed individually in a sealed, sterile packing and is meant for single use only. Packings of several sizes are available. The first apparatus therefore helps to avoid unnecessary opening and hence contamination of several sealed and sterile packings of the second apparatus to determine and select the right size of the circumcision tool for any individual.

It is to be understood that the present invention is not to be limited in its applications or uses to the details of construction and arrangement of parts illustrated in the accompanying drawings, because the present invention (and its inventive concept) is capable of other embodiments, variations and modifications, and of being practised or carried out in various ways. Furthermore, it is to be understood that phraseology and terminology employed herein is for the purpose of description and illustration only, and is not for the purpose of limitation.

Figure 1:
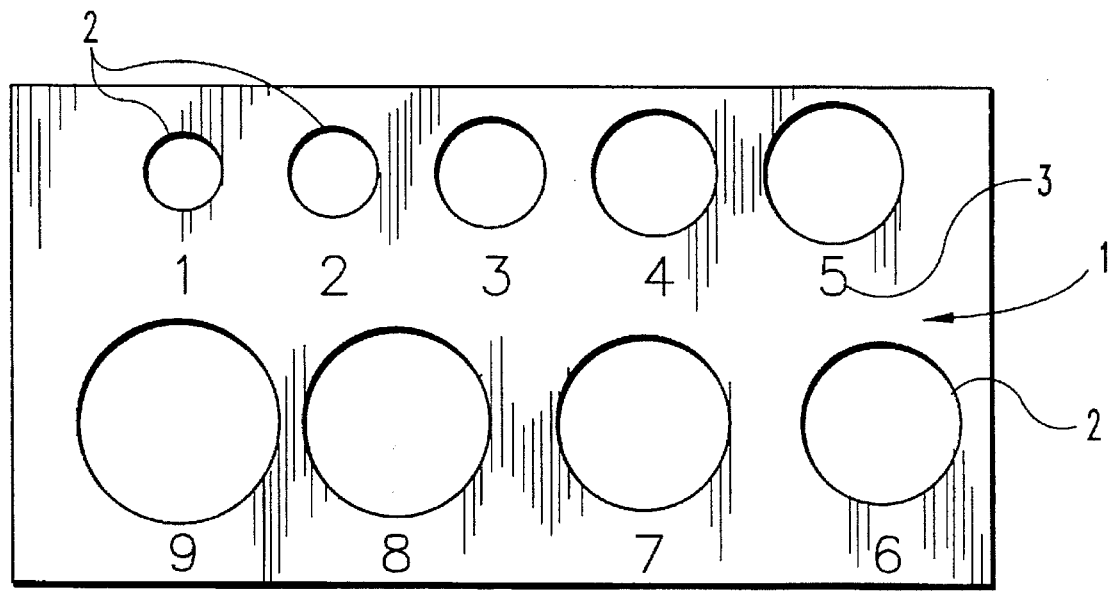
FIG. 1 is a plan view of a measuring device of the present invention.
Figure 2:
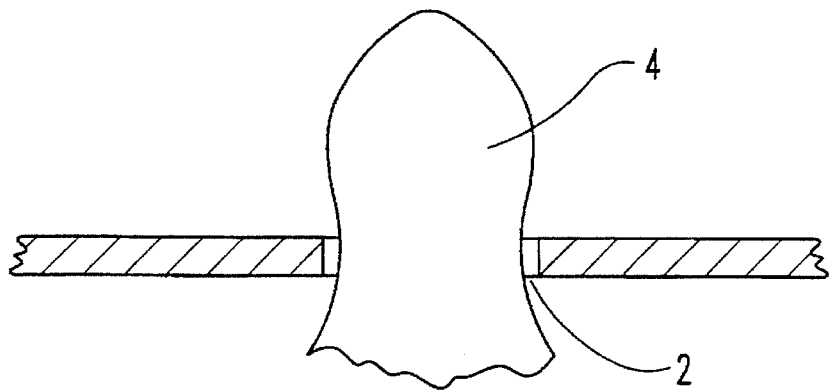
FIG. 2 shows a fragmentary cross-section view of a circular opening of the device of FIG. 1 as it measures the glans penis.

Referring, now, in detail to the drawings, wherein like reference numericals designate like parts in the several figures, FIG. 1 is a flat, rectangular plate 1 having a number of circular openings which are arranged in two rows. These circular openings are of progressively increasing diameters representing the different diameters of the glans penis from infant size to adult size. The edges of the rim 2 of each of the circular openings are smoothly rounded. The size 3 of each circular opening is marked adjacent to it. Each such mark represents the different sizes of the glans. The measuring device is packed separately in a sterile packing. When required for use, it is removed from its packing and attempts are made to pass the circular openings over the exposed glans penis 4 (FIG. 2). That circular opening which allows the glans penis to pass through it, from the tip up to the base of glans, just comfortably, without compressing the glans, is selected as the size appropriate for that particular individual. The size marked on the plate for that particular circular opening is noted and this is then used to select a similarly sized circumcision tool. Thus, the correct size of circumcision tool is selected to perform the circumcision for any individual.

Figure 3:
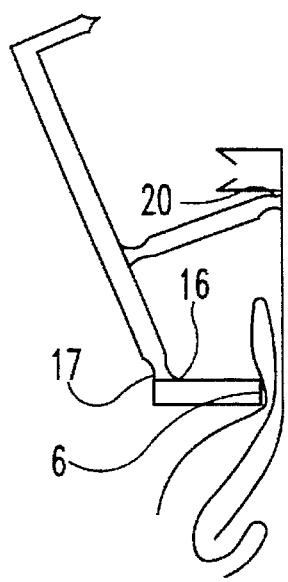
FIG. 3 is a side elevation of the circumcision clamp of the present invention in its unengaged state.
Figure 3:
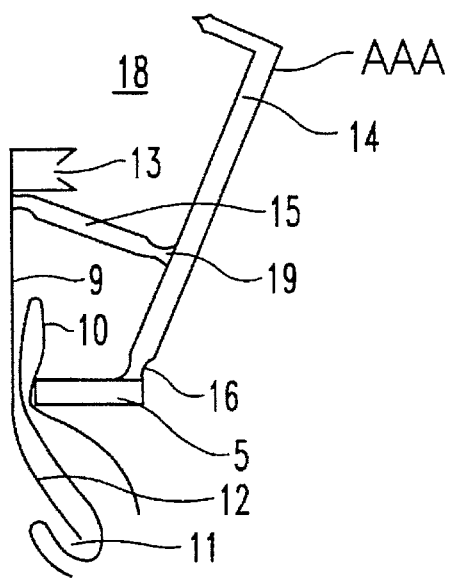

FIG. 3 shows a circumcision clamp according to the invention. Formed entirely of plastic, the instrument consists of outer and inner members connected to each other by means for two levers. The three main parts are described as follows:

(A) The outer member (B) The inner member (C) The levers (A) The outer member 5 is a flat circular plate with a circular opening in the centre. The rim 6 of this opening has a lower tapered annular edge 7 and an upper flat annular edge 8, as shown in FIG. 10.

(B) The inner member 9 is a hollow tube having an enlarged lower portion adapted to receive the glans of the penis inside the tube and to allow the prepuce 10 to fit over the outside of the lower portion of the tube. The lower end of the inner member proximates the base of the glans and is seated near the corona glandis 11. The diameter of the upper end is similar to that of the upper two-thirds of the inner tube while that of the lower one-third which forms the lower portion increases progressively towards the lower end of the inner member so as to form a slight curve 12 as shown in FIG. 3. The outer surface of the lower portion of the inner member mates entirely with the lower tapered annular edge of the rim of the circular opening of the outer member. At diametrically opposed locations on the upper end of the outer surface of the inner member are provided two similar, separate and inflexible catches 13. The inner member 9 is sufficiently elongated to extend slightly beyond the average length of the flaccid glans penis. This allows room for the surgeon to manipulate the positioning of the foreskin over the inner member.

Figure 7:
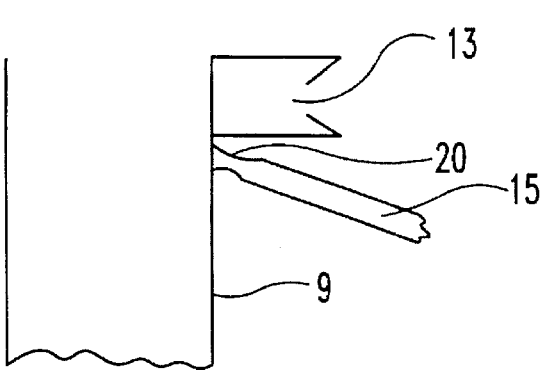
FIG. 7 shows an enlarged fragmentary cross-section view of the design of the flexible hinge joint where one end of the short limb is joined to the inner member.

(C) The circumcision tool is provided with two levers of similar shape and size. Like ends of each lever are attached separately at diametrically opposite similar positions to both the outer and inner members. Each lever consists of a clamping arm 14 and a short limb 15, which are both elongated rectilinear members. Both are rectangularly shaped and their outer and inner surfaces are wide whereas the side surfaces are narrow. The clamping arm 14 extends from the upper surface of the outer member 5 to the upper end of the outer surface of the inner member 9. One end of the clamping arm 14 is joined by a hinge joint 16 to the upper surface of the outer member 5 just on the inside of the edge of the periphery of the outer member. The lower end of the outer surface of the clamping arm 14 proximates the edge of the periphery 17 of the outer member 5. The hinge joint provides a hinge type of movement to the clamping arm. This is made possible by making the narrow surface of the clamping arm slightly more narrower at the end before it joins firmly to the upper surface of the outer member. Such a joint takes advantage of a property of flexibility of plastic, as the entire tool is made of plastic. The other end of the clamping arm is provided with a ratchet 18 on the inner surface, so that when the clamping arms 14 are engaged when a circumcision is performed, each ratchet 18 mates separately with the catches 13 provided on the inner member 9. The ratchets are non-releasable once they are mated with the catches. This prevents reuse of the circumcision clamp after it has dropped off from the glans when the wound has healed. A short limb 15 which also forms a component of the lever is joined to the middle or thereabouts of the inner surface of the clamping arm 14 with a similar hinge joint 19 as shown in FIG. 9. The other end of the short limb 15 is joined to the inner member 9 at its upper end on the outer surface by a similar hinge joint 20 as shown in FIG. 7. This joint is positioned just below the catch means 13 provided on the inner member 9.

Figure 4:
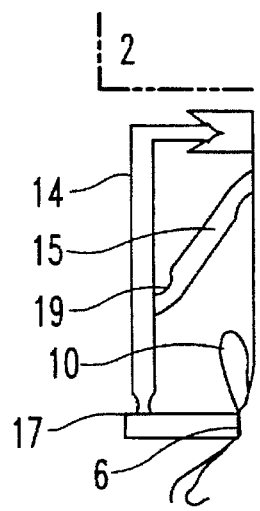
FIG. 4 is a side elevation of the clamp in its engaged state.
Figure 4:
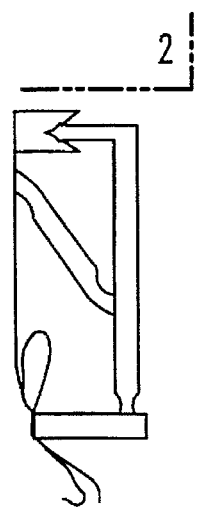
Figure 8:
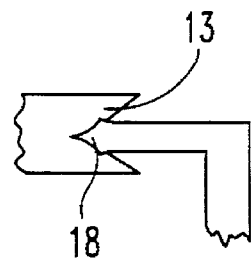
FIG. 8 shows an enlarged fragmentary cross-section view of the mated portion of the catch of the inner member with the ratchet step of the clamping arm.

In operation, as the fingers grip the levers at points AAA, the ratchets 18 (FIG. 3) on the clamping arms 14 are brought towards the catches 13 (FIG. 3) of the inner member. As the clamping arm is moved thus, it exerts a force against the short limb 15, which by virtue of its attachments, as heretofore described, exerts a displacing and guiding force, back to the clamping arm 14 and through it, to the attached outer member 5. Thus, the outer member 5 is also slidably guided over and on the outer side of the inner member 9. Clamping is obtained when the ratchets 18 engage the catches 13 as shown in FIG. 4 and 8. A click will indicate that the outer member 5 has mated with the outer surface of the lower portion of the inner member. In this position, the lower tapered annular edge of the rim of the circular opening of the outer member mates annularly with the outer surface of the lower portion of the inner member. Thus, a prepuce 10 fitted over the inner member 9 is clamped between the outer member 5 and inner member 9.

The mode of performing a circumcision with this instrument will now be described. The prepuce of the subject is prepared, by inserting dorsally a lubricated probe into the potential space between the prepuce and the glans up to the Corona glandis and the mucous membrane is loosened by moving the probe around the glans gently and care taken not to damage the frenulum. The probe is then removed and the prepuce is retracted and the glans is exposed, to ensure that the glans is free of adhesions. The measuring device is now used, and, as heretofore described, the correct size of circumcision tool is selected. The clamping arms 14 of the circumcision tool are first fully extended so that the outer member is positioned near the upper end of the inner member. This allows enough space in which to manipulate the foreskin 10 and the inner member 9 so that the inner member is made to fit between the head of the penis and the foreskin. By applying pressure on the clamping arms, the outer member is now slidably guided on the outside of the foreskin until the outer member is positioned at the desired level of the foreskin, at which the clamping is to be obtained. The clamping arms 14 are then progressively gripped further until the ratchets 18 on the clamping arms have mated with the catches 13 on the inner member and in an instant a click is felt. This indicates that an instant and complete compression and hence complete occlusion of the foreskin has been obtained. The occluded foreskin is then cut off at the level of the upper surface of the outer member using a sharp blade. The entire tool, which is made of plastic and is very light, is then left intact on the penis and does not need any dismantling or any further manipulation. It drops off by itself when the wound has healed in a couple of days.

Alternatively, the occluded foreskin may be left intact and the device will fall off in a few days, leaving a healed circumcision.

In some cases, known as PHIMOSIS the prepuce may be too small to allow insertion of the inner member over the glans and within the prepuce. In such cases it may be necessary to slit the prepuce longitudinally by some means such as a surgical scissors to allow insertion of the inner member over the glans.

Measurement of the circumference of the glans can, of course, be carried out in a number of ways by using a variety of devices such as for example a measuring tape, besides other means which permit modifications without departing from the basic idea of this invention.

The disposable measuring device and the disposable circumcision tool are of such simple design that they can be easily made out of a wide variety of reinforced or unreinforced materials such as polystyrene, aldehyde resins, polypropylene, nylon, polyesters and the like, by such methods as extrusion molding and the like. The clamp can also be made from metals such as stainless steel, aluminium, alloys and the like by casting forging or stamping. The plastic material selected is capable of being sterilised by gamma irradiation or by non-toxic chemicals, thermal sterilisation or by contact with a sterilising solution. It is packed in a sterile, disposable and environment-friendly packing.

I claim:

1. A circumcision clamp comprising a clamping ring of annular shape associated with a tubular support having an open distal end and a flared proximal end section for internal reception of the glans penis and external envelopment by the prepuce, the clamping ring and the tubular support being movable relative to each other between an open position defining a prepuce-receiving gap and a closed position in which the gap is closed, and a locking means for locking the clamping ring in the closed position, wherein the clamp is of lightweight unitary construction and the clamping ring is displaceably mounted on and carried by the tubular support and the distal end of the tubular support permits voiding of urine and enlargement of the penis, such that the clamp is wearable for a few days, and wherein the locking means comprises at least one locking arm hingedly connected to the clamping ring at its one end and provided with a locking formation at its opposite end for locking engagement with a complementary locking formation on said tubular support, and wherein the locking means comprises two locking arms positioned at diametrically opposed sides of the clamping ring.

2. A circumcision clamp comprising a clamping ring of annular shape associated with a tubular support having an open distal end and a flared proximal end section for internal reception of the glans penis and external envelopment by the prepuce, the clamping ring and the tubular support being movable relative to each other between an open position defining a prepuce-receiving gap and a closed position in which the gap is closed, and a locking means for locking the clamping ring in the closed position, wherein the clamp is of lightweight unitary construction and the clamping ring is displaceably mounted on and carried by the tubular support and the distal end of the tubular support permits voiding of urine and enlargement of the penis, such that the clamp is wearable for a few days, and wherein the locking means comprises at least one locking arm hingedly connected to the clamping ring at its one end and provided with a locking formation at its opposite end for locking engagement with a complementary locking formation on said tubular support, and wherein said clamp is made in synthetic plastics material with the hinged connections between each of said locking arms and said clamping ring provided by zones of reduced material thickness.

3. A circumcision clamp comprising a clamping ring of annular shape associated with a tubular support having an open distal end and a flared proximal end section for internal reception of the glans penis and external envelopment by the prepuce, the clamping ring and the tubular support being movable relative to each other between an open position defining a prepuce-receiving gap and a closed position in which the gap is closed, and a locking means for locking the clamping ring in the closed position, wherein the clamp is of lightweight unitary construction and the clamping ring is displaceably mounted on and carried by the tubular support and the distal end of the tubular support permits voiding of urine and enlargement of the penis, such that the clamp is wearable for a few days, and wherein the locking means comprises at least one locking arm hingedly connected to the clamping ring at its one end and provided with a locking formation at its opposite end for locking engagement with a complementary locking formation on said tubular support, and wherein said clamp is made in synthetic plastics material with the hinged connections between each of said locking arms and said clamping ring provided by zones of reduced material thickness, and said clamp being made by a single-shot injection moulding process.

\* \* \* \* \*